（12) United States Patent
Bauer et al.

(10) Patent No.: US 8,822,217 B2
(45) Date of Patent: Sep. 2, 2014

(54) METHOD FOR CULTIVATING TENDON CELLS FROM PLURIPOTENT CELLS OF MESENCHYMAL ORIGIN

(75) Inventors: Hans-Christian Bauer, Österreich (AT); Herbert Tempfer, Österreich (AT)

(73) Assignee: Angewandte Biotechnologie GmbH, Salzburg (AT)

( * ) Notice: Subject to any disclaimer, the term of this patent is extended or adjusted under 35 U.S.C. 154(b) by 1435 days.

(21) Appl. No.: 12/156,804

(22) Filed: Jun. 5, 2008

(65) Prior Publication Data

US 2008/0305546 A1    Dec. 11, 2008

(30) Foreign Application Priority Data

Jun. 6, 2007   (AT) .................................. 888/2007

(51) Int. Cl.
*C12N 5/077*   (2010.01)
*C12N 5/071*   (2010.01)

(52) U.S. Cl.
CPC ............ *C12N 5/066* (2013.01); *C12N 2506/21* (2013.01)
USPC ....................................................... 435/377

(58) Field of Classification Search
None
See application file for complete search history.

(56) References Cited

U.S. PATENT DOCUMENTS

2006/0147426 A1* 7/2006 Schiller et al. ............... 424/93.7
2006/0205071 A1   9/2006 Hasson et al.
2008/0004713 A1   1/2008 Nakamura et al.

FOREIGN PATENT DOCUMENTS

| DE | 10 2005 022 032 | 11/2006 |
|----|-----------------|---------|
| EP | 0 952 792 | 11/1999 |
| WO | WO 96/40866 | 12/1996 |
| WO | WO 2006/029198 | 3/2006 |
| WO | WO 2006/036925 | 4/2006 |

* cited by examiner

*Primary Examiner* — Catherine Hibbert
(74) *Attorney, Agent, or Firm* — Collard & Roe, P.C.

(57) ABSTRACT

A method for cultivating tendon cells from non-embryonic pluripotent cells of mesenchymal origin includes the cultivation of isolated cells in a culture medium under standard culture conditions in a culture vessel. In order to increase the collagen secretion, before their complete confluence, the cells are further cultivated in a culture medium mixed with ascorbic acid and/or ascorbic acid-2-phosphate in a concentration of 25 to 75 μg/ml and are subjected to hyperosmolar treatment in a culture medium whose osmolarity is adjusted to 350 to 500 mosmol/l.

4 Claims, 1 Drawing Sheet

METHOD FOR CULTIVATING TENDON CELLS FROM PLURIPOTENT CELLS OF MESENCHYMAL ORIGIN

CROSS REFERNCE TO RELATED APPLIATIONS

Applicant claims priority under 35 U.S.C. §119 of Austrian Application No. A 888/2007 filled Jun. 6,2007.

1. Field of the Invention

The invention relates to a method for cultivating tendon cells from non-embryonic pluripotent cells of mesenchymal origin, wherein the isolated cells are cultivated in a culture medium under standard culture conditions in a culture vessel.

2. Description of the Prior Art

Tendon cells are responsible for the synthesis and maintenance of the connective tissue between bones and muscles. The cells are enclosed by an extended, three-dimensional network of matrix components which predominantly consist of fibrillar collagens of type I (95% of the tendon material), types III and V, proteoglycans, elastin and fibronectin. These tendon-specific components of the extracellular matrix give the tendons their astonishing strength and dimensional stability. The differentiation of the tendon cells is unclear. It is assumed that they originate from pluripotent cells of mesenchymal origin. These mesenchymal stem cells are descendants of neural crest cells or mesodermal somitic cells and are starting cells for different cell types such as adipocytes, muscle cells, osteoblasts, chondrocytes and even tendon cells. The differentiation into the individual cell classes is controlled by various growth factors.

Under normal physiological conditions, tendons are poorly vascularised and contain mitotically barely active tendon cells. This is considered to be the main reason for the protracted healing of injured tendons. In addition, the quality of the matrix components in injured tendons is poor. Attempts have therefore been made to speed up the healing process by the transplantation of tendon cells in a corresponding matrix. However, the expectations have not been fulfilled.

Another method for producing functional tendon transplants is the culture of precursor cells as the starting point. These precursor cells are obtained from mesenchymal stem cells and are differentiated in vitro using specific growth factors (DE 10 2005 022 032 A1, EP 0 952 792 B1). In order that the cells can be successfully transplanted, however, they should be in an activated state, i.e. they should produce increased collagen, primarily type I collagen which is of particular importance for the tendon function. The use of ascorbic acid and ascorbic acid-2-phosphate is known in this context (DE 10 2005 022 032 A1, WO 1996/040866 A1). In addition, a serum-free culture medium for haematopoietic stem cells based on peptone is known (WO 1996/040866 A1), wherein the osmolality of the solution, which can also contain ascorbic acid, inter alia, is adjusted with the aid of sodium chloride to a value between 232 and 377 mosmol/kg. For the differentiation of stem cells for bone marrow transplantation, it has been proposed (US 2006/0205071 A1) to adjust the osmolality of the culture medium to between 290 and 340 mosmol/kg similarly to the pH. For the cultivation of embryonic stem cells using growth factors for fibroblasts, it is furthermore known (WO 2006/036925 A1) to raise the osmolality of specific culture media which can contain ascorbic acid phosphate, to 340 mosmol/kg with the aid of sodium chloride. Finally, it is reported (WO 2006/029198 A1) that for various culture media, advantageous proliferation ratios for undifferentiated embryonic human stem cells can be maintained at a pH of 7.2, an osmolality of 350 mosmol/kg and an atmosphere containing 10% carbon dioxide and 5% oxygen. However, such prior art does not give any indication of any activation of tendon cells.

SUMMARY OF THE INVENTION

It is therefore the object of the invention to configure a method for cultivating tendon cells from pluripotent cells of mesenchymal origin of the type described initially such that the tendon cells can be transferred in vitro into an advantageous state for transplantation.

The invention achieves the formulated object whereby, prior to their confluence, the cells are further cultivated on the one hand in a culture medium mixed with ascorbic acid and/or ascorbic acid-2-phosphate in a concentration of 25 to 75 μg/ml and on the other hand, exposed to hyperosmolar treatment in a culture medium whose osmolarity is adjusted to 350 to 500 mosmol/l.

Due to the use of ascorbic acid or ascorbic acid-2-phosphate known per se, the collagen production of the cell culture can certainly be stimulated but the activation associated therewith is not sufficient for a promising transplantation. Tendon cells are primarily activated by mechanical loading, which can only be implemented with difficulty in a cell culture. This loading corresponds biophysically to a change in the ionic pressure ratios in the cell, i.e. the osmolarity so that the tensile loadings occurring in the natural healing process can be simulated with the aid of a hyperosmolar treatment. If the osmolarity of the culture medium is enhanced with osmotically active, chemically and biologically inert molecules such as saccharose, mannitol and similar, cell shrinkage comparable to the pressure loading takes place as a result of emergence of water from the cell, bringing about, in addition to a slight increase in collagen secretion, a significant increase in the cross-linking of the extracellular matrix and consequently a considerable improvement in the mechanical properties of a tendon transplant. Since the influence of ionic substances on the osmotic ratios inside a cell depends on their dissociability in the solvent, no controlled simulation of a mechanical cell loading can be brought about by an adjustment of the osmolality unlike the adjustment of the osmolarity in which all anionic parts become uniformly osmotically active.

Although the hyperosmolar treatment of the cells following their stimulation for increased collagen production by ascorbic acid or ascorbic acid-2-phosphate can be carried out if the time interval of these treatments is selected to be sufficiently short, particularly favourable process conditions are obtained during a treatment of the cells with ascorbic acid or ascorbic acid-2-phosphate in a hypersmolarly adjusted culture medium. A preferred osmolarity is 350 to 400 mosmol/l. Usual chemically and biologically inert osmotic substances can be used to adjust the osmolarity. The cultivation of the cells under the required hyperosmolar conditions usually takes place generally during a time interval of 12 to 120 h, preferably 48 to 72 h.

In order to ensure a good proliferation rate, the cells can be cultivated in primary culture under standard culture conditions and passaged before their confluence, the first passage then preferably being cultivated further under standard culture conditions as far as the logarithmic growth phase before the cells are treated with ascorbic acid or ascorbic acid-2-phosphate under hyperosmolar conditions. Standard culture conditions are understood as incubation of the cells in an incubator provided for this purpose at 36 to 38° C., 5% carbon dioxide and a humidity of 95 to 100%. Instead of gasification with carbon dioxide, buffering with HEPES is selected.

Stimulation of the cells having a very low passage number, preferably of the first passage, to enhanced collagen production under hyperosmolar conditions additionally helps to prevent de-differentiation of the cells. In this connection it should be noted that the differentiation of the pluripotent mesenchymal cells under standard culture conditions can be carried out with the aid of ascorbic acid or ascorbic acid-2-phosphate without using transforming growth factors, allowing the cultivation of genetically non-manipulated tendon cells as an advantageous requirement for autologous transplants although the use of corresponding growth factors during the cultivation of mesenchymal precursor cells is in no way excluded for particular cases of use.

Exemplary Embodiment

In order to isolate pluripotent cells of mesenchymal origin, small pieces of Substantia spongiosa, biopsied from the human wing of ilium were digested at 37° C. in 2 ml of DMEM (Dulbecco's modified eagles medium with 4.5 g/l of glucose) with 2.5 mg/ml collagenase for 3 h. The cell pellet obtained from the digested pieces by multiple centrifugation was inoculated in a density of 200000 cells/cm$^2$ and was incubated for 24 h in DMEM with 10% foetal calf serum (FCS) and specifically at 37° C., 5% $CO_2$ and 100% humidity. One preparation gives a growth area of 60 to 180 cm$^2$. The culture medium was changed twice a week. Before the cells are confluent after six days, they are passaged in the usual way. The first passage is cultivated further under the standard conditions described until the logarithmic growth phase is reached after three days. The culture medium is then exchanged for a medium which was adjusted to an osmolarity of 360 mosmol/l with the aid of saccharose and, in addition to DMEM mixed with 10% FCS, contains 50 µg/ml of ascorbic acid-2-phosphate. The cells are incubated for four days in this culture medium. The treatment with ascorbic acid-2-phosphate under hyperosmolar conditions leads to a change in the cellular phenotype: the cells become fibroblastic as is to be expected for tendon cells. In addition, the secretion of type I collagen and its cross-linking increases. Following stimulation of the cells to enhanced collagen secretion under hyperosmolar conditions, they are cultivated in a standard culture medium for a further 12 h in order to then be investigated.

BRIEF DESCRIPTION OF THE DRAWING

The results of the investigations are illustrated in the drawings. In the figures

DESCRIPTION OF THE PREFERRED EMBODIMENT

Figure 1:
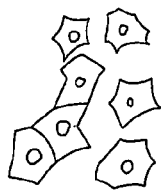
FIG. 1 shows the cell culture before its treatment with ascorbic-2-phosphate in a schematic diagram.
Figure 2:
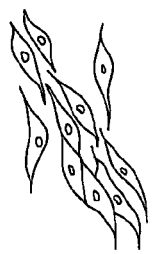
FIG. 2 shows the cell culture following its treatment with ascorbic-2-phosphate in a diagram corresponding to FIG. 1

As can be seen from FIG. 1, the cells show a polygonal structure before their treatment with ascorbic-2-phosphate. As a result of the treatment with ascorbic-2-phosphate, the fibroblastic structures indicated in FIG. 2 are achieved such as are required for tendon cells without transforming growth structures needing to be used for this purpose, so that the cells are not subjected to any genetic treatment.

Figure 3:
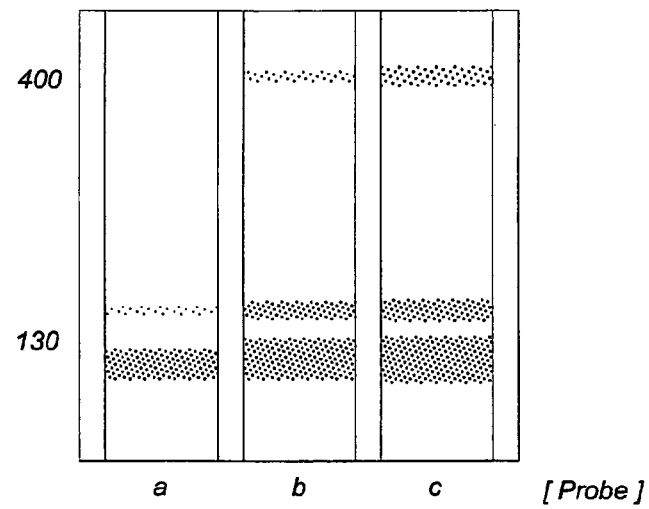
FIG. 3 shows a Western Blot analysis of a cell culture before its treatment with ascorbic-2-phosphate, following its treatment with ascorbic-2-phosphate and following a treatment with ascorbic-2-phosphate under hyperosmolar conditions.

FIG. 3 shows schematically the result of a Western Blot analysis for the collagen production, wherein sample a relates to a cell culture without any treatment with ascorbic-2-phosphate, sample b relates to a cell culture with treatment by ascorbic-2-phosphate and sample c relates to a cell culture with treatment by ascorbic-2-phosphate under hyperosmolar conditions. A significant increase in the secretion of type I collagen can be seen for samples b and c, this being apparent from the double band in the area of the molecular mass of 130 kD. Compared to sample b, sample c which was treated under hyperosmolar conditions shows enhanced cross-linking of the collagen in the area of 400 kD due to the elevated osmolarity of the culture medium. As a result of this cross-linking, sample c is more resistant to digestion with pepsin.

The invention claimed is:

1. A method for cultivating tendon cells from non-embryonic pluripotent cells of mesenchymal origin, the method comprising the steps of:
cultivating isolated non-embryonic pluripotent cells of mesenchymal origin in a culture medium under standard culture conditions in a culture vessel;
before a complete confluence of the cultivated non-embryonic pluripotent cells of mesenchymal origin, further cultivating the cultivated non-embryonic pluripotent cells of mesenchymal origin in a culture medium mixed with ascorbic acid and/or ascorbic acid-2-phosphate in a concentration of 25 to 75 µg/ml; and
before a complete confluence of the cultivated non-embryonic pluripotent cells of mesenchymal origin, subjecting the cultivated non-embryonic pluripotent cells of mesenchymal origin to hyperosmolar treatment in a culture medium whose osmolarity is adjusted to 350 to 500 mosmol/l using chemically and biologically inert osmotic substances.

2. The method according to claim 1, wherein the hyperosmolar treatment of the non-embryonic pluripotent cells of mesenchymal origin and the further cultivation with ascorbic acid or ascorbic acid-2-phosphate takes place simultaneously.

3. The method according to claim 1, wherein the hyperosmolar treatment of the non-embryonic pluripotent cells of mesenchymal origin takes place in a culture medium whose osmolarity is adjusted to 350 to 400 mosmol/l.

4. The method according to claim 2, further comprising the steps of:
passaging the cultivated isolated non-embryonic pluripotent cells of mesenchymal origin before confluence of the cultivated isolated non-embryonic pluripotent cells of mesenchymal origin; and
further cultivating the passaged non-embryonic pluripotent cells of mesenchymal origin under standard culture conditions as far as a logarithmic growth phase before the non-embryonic pluripotent cells of mesenchymal origin undergo the simultaneous treatments of ascorbic acid or ascorbic acid-2-phosphate and hyperosmolar conditions.

* * * * *